US010925470B2

(12) United States Patent
Okaniwa et al.

(10) Patent No.: US 10,925,470 B2
(45) Date of Patent: Feb. 23, 2021

(54) ENDOSCOPE SYSTEM HAVING FIRST AND SECOND ENDOSCOPES WITH INSERTION SECTIONS HAVING DIFFERENT HARDNESS VARIATION AMOUNTS

(71) Applicant: OLYMPUS CORPORATION, Tokyo (JP)

(72) Inventors: Suguru Okaniwa, Hachioji (JP); Seisuke Takase, Hachioji (JP); Hidehiro Joko, Hachioji (JP); Isamu Nakajima, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 377 days.

(21) Appl. No.: 15/971,050

(22) Filed: May 4, 2018

(65) Prior Publication Data

US 2018/0249892 A1 Sep. 6, 2018

Related U.S. Application Data

(63) Continuation of application No. PCT/JP2016/083424, filed on Nov. 10, 2016.

(30) Foreign Application Priority Data

Nov. 13, 2015 (JP) ................................ JP2015-223174

(51) Int. Cl.
*A61B 1/005* (2006.01)
*A61B 1/00* (2006.01)
(Continued)

(52) U.S. Cl.
CPC ............ *A61B 1/0055* (2013.01); *A61B 1/005* (2013.01); *A61B 1/0011* (2013.01);
(Continued)

(58) Field of Classification Search
USPC .................................................. 600/144, 113
See application file for complete search history.

(56) References Cited

U.S. PATENT DOCUMENTS 3,854,473 A * 12/1974 Matsuo ................ A61B 1/2736
600/104
6,203,494 B1 * 3/2001 Moriyama ........... A61B 1/0052
600/144
(Continued)

FOREIGN PATENT DOCUMENTS

EP 2702925 A1 3/2014
JP 2004121860 A 4/2004
(Continued)

OTHER PUBLICATIONS

International Search Report dated Jan. 31, 2017 issued in PCT/JP2016/083424.

*Primary Examiner* — Michael J Carey
*Assistant Examiner* — Minqiao Huang
(74) *Attorney, Agent, or Firm* — Scully, Scott, Murphy & Presser, P.C.

(57) ABSTRACT

An endoscope system sets a hardness variation of a thick flexible tube portion and a hardness variation of a thin flexible tube portion such that their respective ratios against base hardness are constant, and as each flexible tube portion becomes thicker, the hardness variation increases and an endoscope with a relatively thin flexible tube portion has a smaller hardness variation. This makes it possible to avoid situations like an endoscope with a thick flexible tube portion lacking hardness or an endoscope with a thin flexible tube portion becoming too hard, and makes it possible to perform optimum insertion operation in accordance with the thickness of a flexible tube.

2 Claims, 7 Drawing Sheets

(51) Int. Cl.
*A61B 1/01* (2006.01)
*G02B 23/24* (2006.01)
*A61B 1/012* (2006.01)
*A61B 1/018* (2006.01)
*A61B 1/273* (2006.01)

(52) U.S. Cl.
CPC ............ *A61B 1/00078* (2013.01); *A61B 1/01* (2013.01); *A61B 1/0125* (2013.01); *G02B 23/24* (2013.01); *A61B 1/018* (2013.01); *A61B 1/273* (2013.01)

(56) References Cited

U.S. PATENT DOCUMENTS

| | | | |
|---|---|---|---|
| 2012/0053417 A1* | 3/2012 | Yamakawa | A61B 1/00078 600/144 |
| 2012/0071722 A1* | 3/2012 | Nakamura | A61B 1/00078 600/140 |
| 2013/0150666 A1* | 6/2013 | Otawara | G02B 23/2423 600/104 |
| 2014/0039259 A1 | 2/2014 | Okaniwa | |
| 2015/0087905 A1* | 3/2015 | Ueda | A61B 1/005 600/109 |
| 2015/0272425 A1* | 10/2015 | Ueda | A61B 1/00078 600/144 |

FOREIGN PATENT DOCUMENTS

| | | | | |
|---|---|---|---|---|
| JP | 2012081011 A | * | 4/2012 | ......... A61B 1/00078 |
| JP | 2012081011 A | | 4/2012 | |
| WO | 2013172089 A1 | | 11/2013 | |

* cited by examiner

ENDOSCOPE SYSTEM HAVING FIRST AND SECOND ENDOSCOPES WITH INSERTION SECTIONS HAVING DIFFERENT HARDNESS VARIATION AMOUNTS

CROSS REFERENCE TO RELATED APPLICATION

This application is a continuation application of PCT/JP2016/083424 filed on Nov. 10, 2016 and claims benefit of Japanese Application No. 2015-223174 filed in Japan on Nov. 13, 2015, the entire contents of which are incorporated herein by this reference.

BACKGROUND OF THE INVENTION

1. Field of the Invention

The present invention relates to an endoscope system provided with a hardness change mechanism configured to change hardness of an insertion portion.

2. Description of the Related Art

In recent years, endoscopes have been widely used, which can observe a region to be inspected in a subject by inserting an elongated insertion portion into the subject and perform, if necessary, therapeutic treatment using a treatment instrument.

The insertion portion of the endoscope is configured with a flexible tube having flexibility so as to be insertable even into a bent insertion path connected to a rigid portion at a distal end, but because of this flexibility, the azimuth on the distal end side may not be determined with respect to the hand side, making it difficult to introduce the flexible tube toward a target direction.

For this reason, an endoscope provided with a hardness change mechanism (hardness variable means) is provided which incorporates in the flexible tube, a pipe-shaped coil and a wire for pulling the coil, and can change hardness of the flexible tube by pulling the wire and compressing the coil.

For example, Japanese Patent Application Laid-Open Publication No. 2004-121860 discloses an endoscope system provided with a plurality of endoscopes with insertion portions having different lengths, a flexible portion of each endoscope including hardness variable means for increasing hardness in accordance with an amount of bending in a rigid state. The hardness variable means disclosed in Japanese Patent Application Laid-Open Publication No. 2004-121860 is set such that when the insertion portion is in a straight state, a hardness variable width of an endoscope with a long insertion portion becomes smaller than a hardness variable width of an endoscope with a short insertion portion.

SUMMARY OF THE INVENTION

An endoscope system according to an aspect of the present invention includes a first endoscope provided with a flexible first insertion portion and a first hardness change mechanism provided to be operable within the first insertion portion by operating a first hardness operation portion provided on a proximal end side of the first insertion portion and enabled to change hardness of the first insertion portion between a first minimum hardness and a first maximum hardness, and a second endoscope provided with a second flexible insertion portion and a second hardness change mechanism provided to be operable within the second insertion portion by operating a second hardness operation portion provided on a proximal end side of the second insertion portion and enabled to change hardness of the second insertion portion between a second minimum hardness which is greater than the first minimum hardness and a second maximum hardness which is greater than the first maximum hardness, in which the first hardness change mechanism and the second hardness change mechanism are each constructed of a coil pipe, a wire inserted into the coil pipe, a distal end side of the wire being fixed to the coil pipe, and a pulling mechanism configured to contract the coil pipe, in which a proximal end side of the wire is pulled by the hardness operation portion, and by adjusting at least one of a coil diameter of the coil pipe, an elemental wire diameter of the coil pipe, a wire diameter of the wire and a pulling amount of the wire, a hardness variation when the hardness of the second insertion portion is changed from the second minimum hardness to the second maximum hardness is set to be greater than a variation when the hardness of the first insertion portion is changed from the first minimum hardness to the first maximum hardness.

DETAILED DESCRIPTION OF THE PREFERRED EMBODIMENT

Hereinafter, an embodiment of the present invention will be described with reference to the accompanying drawings.

Figure 1:
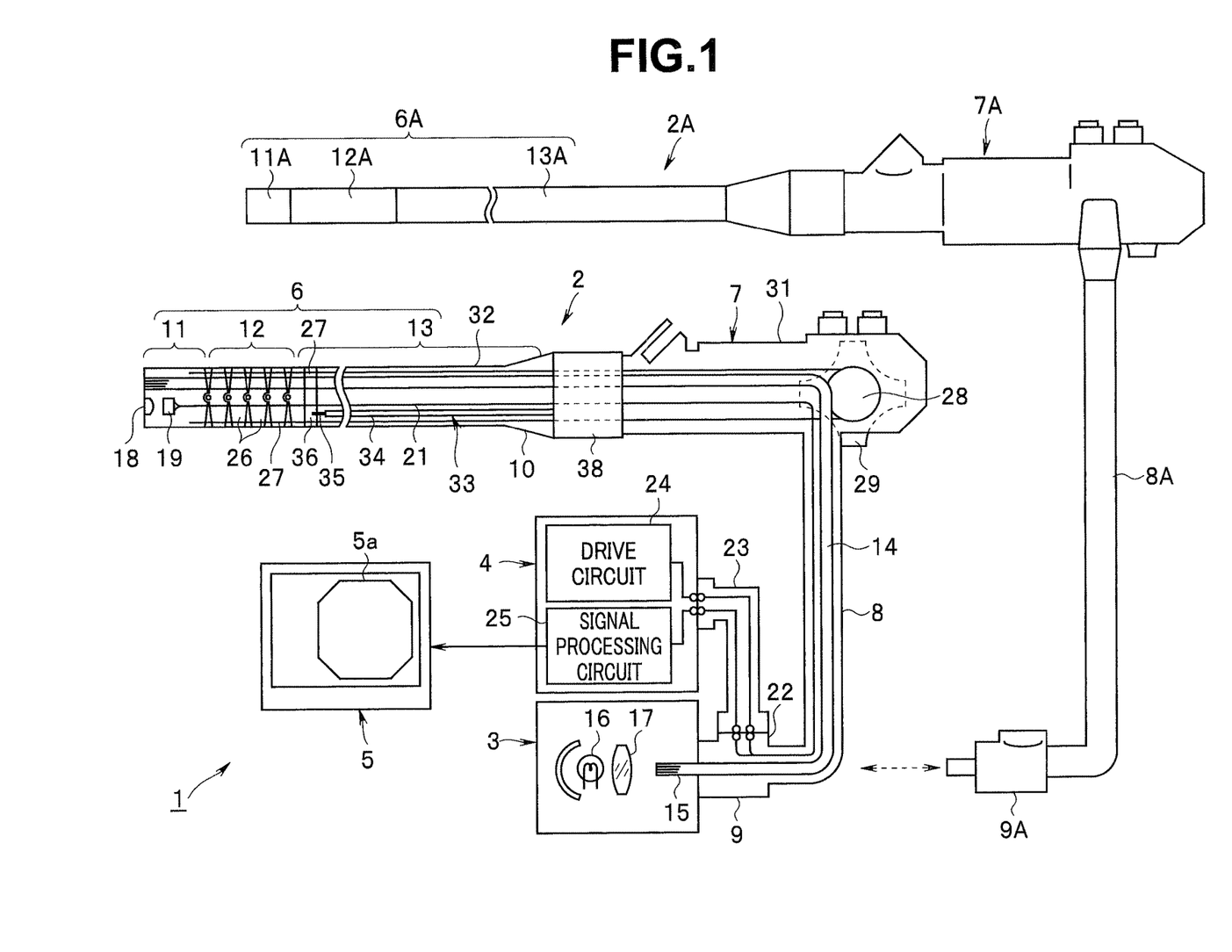
FIG. 1 is a schematic configuration diagram of an endoscope system.

An endoscope system 1 shown in FIG. 1 is provided with an endoscope 2 including an insertion portion 6 formed into an elongated shape, a light source apparatus 3 configured to supply illumination light to the endoscope 2, a signal processing apparatus 4 configured to perform signal processing on an image pickup signal outputted from the endoscope 2 and a monitor 5 configured to display a video signal outputted from the signal processing apparatus 4 on a screen.

The endoscope 2 is provided with the elongated insertion portion 6, a large-width operation portion 7 connected to a rear end side of the insertion portion 6 and a universal cable 8 extending from a side portion of the operation portion 7. A connector 9 is provided at an end of the universal cable 8 and the endoscope 2 can be detachably connected to the light source apparatus 3 and the signal processing apparatus 4 via the connector 9.

The insertion portion 6 is constructed of, from a distal end side, a rigid distal end portion 11, a freely bendable bending portion 12 formed at a rear end of the distal end portion 11 and a long and flexible tube portion 13 formed at a rear end of the bending portion 12, and the rear end side of the flexible tube portion 13 is connected to a front end side of the operation portion 7. A tapered bend preventing member 10 having a bend preventing function is provided on an outer circumference at the rear end of the flexible tube portion 13.

Furthermore, in addition to the endoscope 2, the endoscope system 1 includes a plurality of types of endoscopes such as an endoscope 2A having a similar function. As will be described later, the endoscope 2 is provided with a hardness change mechanism 50 (see FIG. 2) capable of changing hardness (flexibility) of the flexible tube portion 13 constituting a part on the proximal end side of the insertion portion 6 and a cylindrical hardness adjusting knob 38 is turnably provided at the front end portion of the operation portion 7 as a hardness operation portion for a hardness change operation. The other endoscope such as endoscope 2A is likewise provided with a hardness change mechanism, but is different from the endoscope 2 in the thickness of the flexible tube portion 13.

In comparison with the endoscope 2, FIG. 1 illustrates the endoscope 2A as a representative of a plurality of other endoscopes. The basic configuration of the endoscope 2A is similar to the configuration of the endoscope 2, and an operation portion 7A, a universal cable 8A and a connector 9A of the endoscope 2A have configurations similar to the configurations of the endoscope 2, whereas a thickness (outer diameter) of an insertion portion 6A (distal end portion 11A, bending portion 12A and flexible tube portion 13A) is different from the thickness of the insertion portion 6 of the endoscope 2.

The fact that flexible tube portions 13 and 13A of the endoscopes 2 and 2A have different thicknesses means that the flexible tube portions 13 and 13A have different levels of hardness (flexibility against bending) and generally, the flexible tube portion becomes harder as it becomes thicker. Here, it is assumed that the flexible tube portion 13A of the endoscope 2A is relatively thinner and relatively less hard than the flexible tube portion 13 of the endoscope 2.

Note that FIG. 1 illustrates an example in which the connectors 9 and 9A are interchangeable with each other and the endoscope 2 or 2A is selectively connected to the light source apparatus 3 and the signal processing apparatus 4 as common external apparatuses. However, the endoscopes 2 and 2A may be connected to different external apparatuses respectively and the present endoscope system 1 also includes the external apparatuses as well.

Since the endoscopes 2 and 2A basically have similar configurations, the configuration of the endoscope 2 will be mainly described below.

The endoscope 2 allows insertion of a light guide 14 made up of a flexible fiber bundle configured to transmit illumination light through the insertion portion 6, the operation portion 7 and the universal cable 8. The proximal end portion of the light guide 14 is fixed to a light guide connector portion 15 provided so as to protrude from the connector 9 and by connecting the light guide connector portion 15 to the light source apparatus 3, illumination light of a lamp 16 in the light source apparatus 3 is condensed by a lens 17, supplied to an end face of the light guide connector portion 15 and the illumination light is transmitted through the light guide 14 to the distal end side of the insertion portion 6.

The illumination light transmitted through the light guide 14 is emitted forward from the distal end face fixed to an illumination window of the distal end portion 11 to illuminate a subject such as an affected part. An optical image of the illuminated subject is formed at an image forming position through an objective lens 18 attached to an observation window provided at the distal end portion 11 adjacent to an illumination window. An image pickup device 19 made up of a CCD, a CMOS or the like is disposed at the image forming position where the optical image is converted to an electric signal.

The image pickup device 19 is connected to one end of a signal cable 21. The signal cable 21 is inserted through the insertion portion 6 or the like, a rear end of the signal cable 21 is connected to an electric connector 22 of the connector 9 and connected to the signal processing apparatus 4 via an external cable 23. The signal processing apparatus 4 generates a drive signal for driving the image pickup device 19 through a drive circuit 24, and when the drive signal is applied to the image pickup device 19, a photoelectrically converted image pickup signal is read and inputted to a signal processing circuit 25 in the signal processing apparatus 4. The signal processing circuit 25 converts the image pickup signal to a standard video signal and outputs the video signal to the monitor 5. The monitor 5 displays an image of the subject in an endoscope image display region 5a based on the inputted video signal.

The bending portion 12 provided adjacent to the distal end portion 11 is constructed of many ring-shaped bending pieces 26 turnably connected to the adjacent bending pieces 26 at corresponding positions in the vertical and horizontal directions using rivets or the like. A bending operation wire 27 is fixed to a most distal bending piece 26 or the distal end portion 11 and a rear end side of the bending operation wire 27 is connected to a sprocket 28 in the operation portion 7.

A bending operation knob 29 configured to perform a bending operation is attached to a shaft of the sprocket 28. (For simplicity, FIG. 1 illustrates an overview of the bending mechanism with only the vertical or horizontal direction.) By turning the bending operation knob 29, one of a pair of bending operation wires 27 disposed along the vertical direction or the horizontal direction is pulled and the other is loosened so as to allow the bending portion 12 to bend toward the pulled bending operation wire 27 side.

A grasping portion 31 is provided more forward than the position of the operation portion 7 at which the bending operation knob 29 is provided so as to allow a surgeon to operate the bending operation knob 29 with one hand (a finger such as the thumb not used for grasping) grasping the grasping portion 31.

Next, the hardness change mechanism 50 configured to change hardness (flexibility) of the flexible tube portion 13 constituting the proximal end side of the insertion portion 6 will be described with reference to FIG. 1 and FIG. 2. Note that the hardness change mechanism 50 basically has the same configuration for the plurality of endoscopes 2, 2A and the like, but has different actual hardness-related settings of the respective sections as will be described later.

The hardness change mechanism 50 of the endoscope 2 is constructed of a hardness (flexibility) variable member 33 made of an elongated member inserted through a flexible tube 32 that forms an outer skin (shell) of the flexible tube portion 13 and a pulling mechanism 46 configured to pull and contract the hardness variable member 33. The pulling mechanism 46 is provided in the operation portion 7 and configured to pull/contract the hardness variable member 33 in accordance with a turning operation of the hardness adjusting knob 38.

More specifically, the hardness variable member 33 is provided with a pipe-shaped densely wound metallic coil pipe 34 and a flexible pulling wire 35 inserted through the coil pipe 34. A distal end of the pulling wire 35 is firmly fixed to an inner wall of a rigid, ring-shaped connection tube 36 configured to connect the bending portion 12 and the flexible tube portion 13 by means of brazing or the like.

Figure 2:
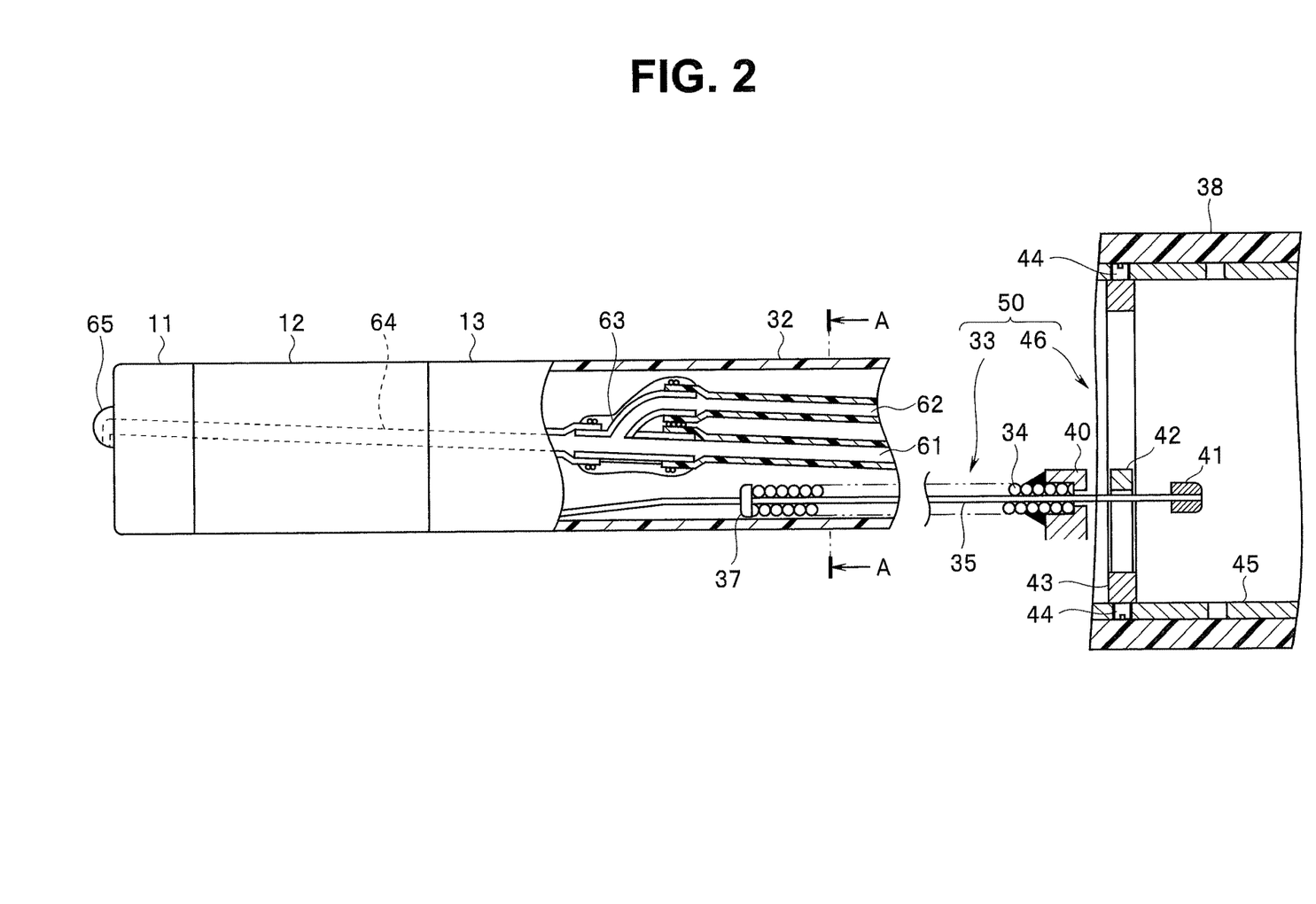
FIG. 2 is an explanatory diagram illustrating a hardness change mechanism of the endoscope.

As shown in FIG. 2, the distal end side of the coil pipe 34 is firmly fixed to the pulling wire 35 via a cap 37 by means of brazing or the like and the distal end of the pulling wire 35 extending from the cap 37 is fixed to the connection tube 36. That is, the distal end of the hardness variable member 33 composed of the coil pipe 34 and the pulling wire 35 is fixed to the connection tube 36 to thereby prevent the coil pipe 34 and the pulling wire 35 from getting tangled with other internal components and damaging the other internal components.

Note that for the distal end portion of the pulling wire 35 extending from the cap 37, a wire different from the pulling wire 35 may be fixed to the inside of the cap 37 and made to extend, and the distal end of the different wire may be fixed to the connection tube 36.

On the other hand, the rear end side of the coil pipe 34 is firmly fixed, by means of brazing or the like, to a coil stopper 40 fixed to a pipe sleeve (not shown) whereby the rear end of the flexible tube 32 is fixed to the operation portion 7. The pulling wire 35 inserted through the coil pipe 34 is made to pass through a hole provided in the coil stopper 40 and extend toward the rear side, and an end portion on the hand side, that is, the rear end portion of the pulling wire 35 is firmly fixed to the ring-shaped wire stopper 41 by means of brazing or the like.

The pulling mechanism 46 configured to pull and contract the hardness variable member 33 is mainly constructed of a pulling member 42 configured to be movable in a horizontal direction by allowing insertion of the pulling wire 35 between a coil stopper 40 and a wire stopper 41, and a cam cylindrical body 45 configured to cause the pulling member 42 in an axial direction. In the present embodiment, the pulling member 42 is fixed to an inner surface of a cylindrical moving ring 43 and the moving ring 43 engages with the cam cylindrical body 45 fixed to the inside of the hardness adjusting knob 38 via two pins 44.

Figure 3:
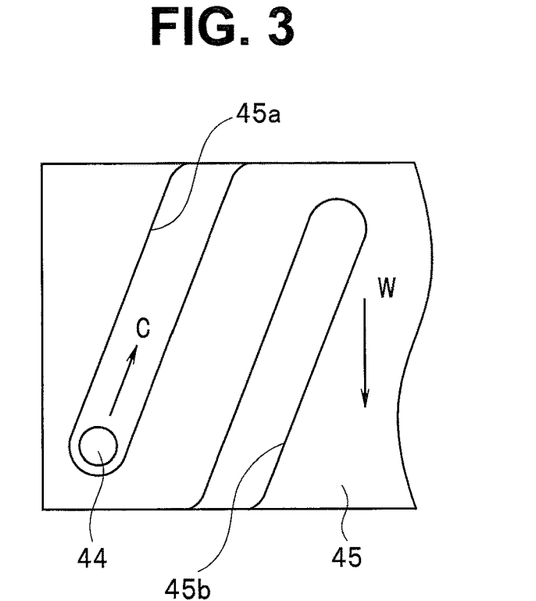
FIG. 3 is an explanatory diagram illustrating an example of shape of a cam groove.

As shown in FIG. 3, cam grooves 45a and 45b are spirally provided at two locations opposite to each other of the cylindrical portion. The cam grooves 45a and 45b have the same shape, and are provided at positions symmetric with respect to an axis of the cam cylindrical body 45, one position overlapping the other position corresponding to the first position turned by 180 degrees. In FIG. 3, the cam grooves 45a and 45b are formed into a simple smooth groove shape (smooth spiral shape).

Note that a recessed part may be provided in the middle or at an end of the cam groove so as to give click sensing to the operator when the pin 44 engages with the recessed part.

When the cam cylindrical body 45 is turned toward a direction shown by reference character W in FIG. 3 by turning the hardness adjusting knob 38, the pin 44 moves through the cam grooves 45a and 45b in a direction shown by an arrow C in FIG. 3, which causes the pulling member 42 to move backward. When the pulling member 42 moves slightly, it eventually hits the wire stopper 41. While the wire stopper 41 is in a condition in which it cannot move backward, the coil pipe 34, the backward movement of which is restricted by the coil stopper 40 is in a most flexible state, that is, in a condition with base hardness in which the wire is most easily bendable.

When the cam cylindrical body 45 is further turned and the pulling member 42 moves backward, the pulling wire 35 is pulled, and a compressive force applies to the coil pipe 34, the coil pipe 34 is hardened and the flexible tube portion 13 can be hardened. That is, when the pulling member 42 moves backward and the rear end of the pulling wire 35 also moves backward simultaneously, the coil stopper 40 relatively acts so as to push the coil pipe 34 forward.

That is, adding a force that causes the rear end of the pulling wire 35 to move backward gives a compressive force to the coil pipe 34, and the compressive force makes it possible to change the flexibility state of the elastic coil pipe 34 to a low flexibility state, that is, a rigid state in which hardness (more accurately, hardness against bending) is high and the coil pipe is less flexible. In this case, it is possible to adjust the magnitude of the compressive force to the coil pipe 34 according to the amount of backward movement of the wire stopper 41 and make variable the flexible tube portion 13 from a base hardness condition in which it is easiest to bend the flexible tube portion 13 to a maximum hardness condition in which it is most difficult to bend the flexible tube portion 13.

Returning to FIG. 2, an air feeding pipeline 61 and a water feeding pipeline 62 are inserted through the insertion portion 6 and the pipelines 61 and 62 converge into one air/water feeding pipeline 64 via a branching member 63 at a position closer to the distal end side than the distal end of the coil pipe 34. A nozzle 65 which is open toward the outer surface of the objective lens 18 is provided at a distal end of the air/water feeding pipeline 64.

Figure 4:
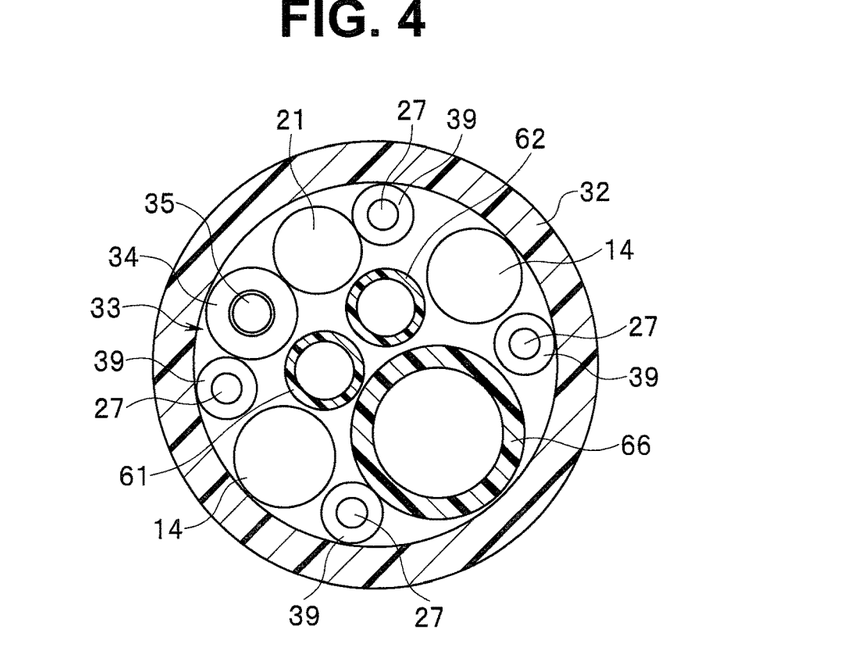
FIG. 4 is a cross-sectional view along a line A-A in FIG. 2.

As shown, for example, in FIG. 4, various internal components are arranged in the insertion portion 6. That is, four bending operation wires 27 disposed at positions corresponding to upper, lower, left and right parts, two light guides 14 disposed diagonally closer to the upper part and diagonally closer to the lower part, a treatment instrument channel 66 disposed closer to the lower part, the coil pipe 34 and the pulling wire 35 disposed closer to the left part, the air feeding pipeline 61 and the water feeding pipeline 62 disposed adjacent to the coil pipe 34 and the pulling wire 35, and the signal cable 21 are arranged. Note that the bending operation wires 27 are guided by guide pipes 39.

Next, an example of an insertion operation method when conducting an endoscope inspection, for example, a large intestine inspection using the endoscope 2 will be described.

Figure 5A:
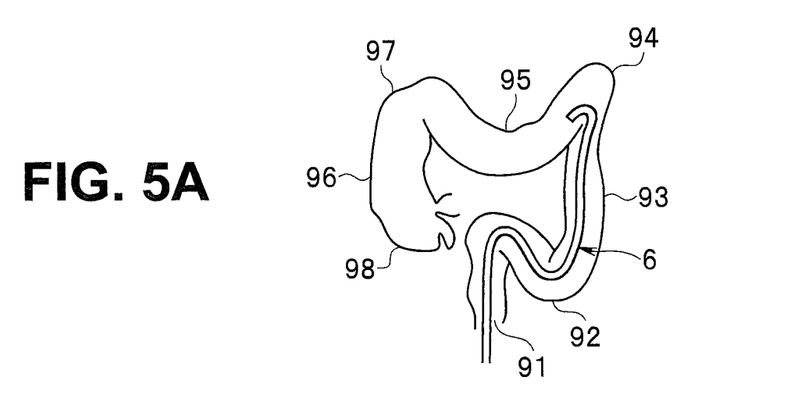
FIG. 5A is an explanatory diagram illustrating the endoscope inserted into a large intestine.

First, as shown in FIG. 5A, (the flexible tube portion 13 of) the insertion portion 6 of the endoscope 2 in a flexible state is inserted from an anus 91 and caused to pass through a sigmoid colon 92 with little pain. At that time, the flexible tube portion 13 also passes through the sigmoid colon 92 while bending. The distal end of the endoscope reaches the vicinity of a splenic flexure 94 from a descending colon 93.

Figure 5B:
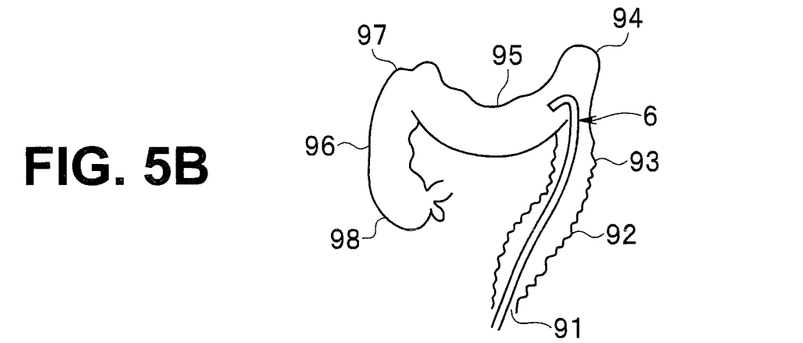
FIG. 5B is an explanatory diagram illustrating the endoscope inserted into a large intestine.
Figure 5C:
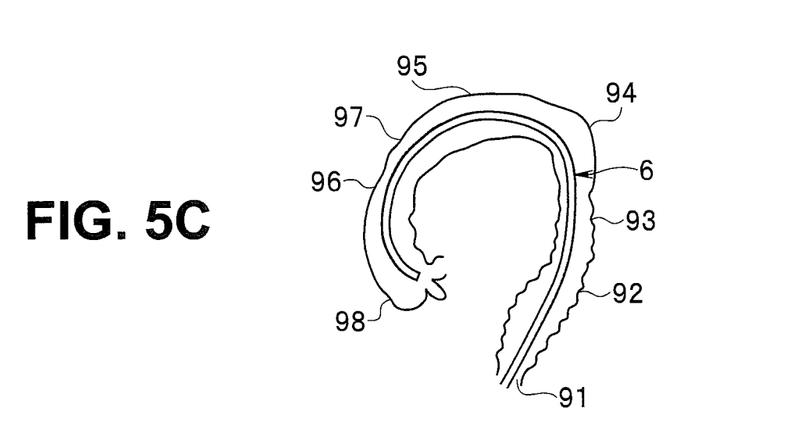
FIG. 5C is an explanatory diagram illustrating the endoscope inserted into a large intestine.

Here, by pulling the flexible tube portion 13 into a substantially linear shape, the sigmoid colon 92 becomes a substantially linear shape as shown in FIG. 5B. In this condition, the hardness adjusting knob 38 is turned to harden the flexible tube portion 13. Then, as shown in FIG. 5C, without the sigmoid colon 92 bending again, the distal end of the endoscope can speedily pass through a transverse colon 95, a hepatic flexure 97 and an ascending colon 96, and reach an appendix 98.

Without hardening the flexible tube portion 13, the sigmoid colon 92 and the transverse colon 95 may bend considerably and the distal end cannot readily move forward, but by hardening the flexible tube portion 13, it is possible to minimize the bending in the sigmoid colon 92 and the transverse colon 95, facilitate the transmission of a hand-side operation to the distal end, allowing speedy insertion of the flexible tube portion 13 to the depth of the large intestine.

In this case, an endoscope is selected from among different types of endoscopes with the flexible tube portion of the insertion portion having different levels of hardness (thickness) depending on the gender and figures of the patient or the presence or absence of adhesion or the like, and the insertion operation method also differs depending on the thickness of the flexible tube. For this reason, in the present endoscope system 1, a plurality of types of the endoscopes such as the endoscopes 2 and 2A with flexible tube portions having different thicknesses are configured to optimize a hardness variation of the flexible tube portion by the hardness change mechanism 50 in accordance with the thickness of the flexible tube portion. In this way, no matter which endoscope may be selected from among endoscopes with flexible tube portions having different thicknesses, it is possible to obtain optimum insertion performance without causing unnatural feeling caused by differences in feeling of use.

More specifically, the hardness variation from base hardness to maximum hardness of the flexible tube portion is set so as to become a variation proportional to the base hardness defined in accordance with the outer diameters of the respective flexible tubes among a plurality of endoscopes with flexible tube portions having different thicknesses. In other words, the respective components of the hardness change mechanism 50 are set such that the hardness of the flexible tube portion increased by the hardness change mechanism 50 is in direct proportion to the hardness before a change determined in accordance with the outer diameters of the respective flexible tubes.

The plurality of endoscopes with flexible tube portions having different outer diameters will be described using the endoscopes 2 and 2A as representatives. As described above, in the present embodiment, the flexible tube portion 13 of the endoscope 2 has a greater outer diameter than the outer diameter of the flexible tube portion 13A of the endoscope 2A, and the base hardness of the flexible tube portion 13 is higher than the base hardness of the flexible tube portion 13A.

Figure 6A:
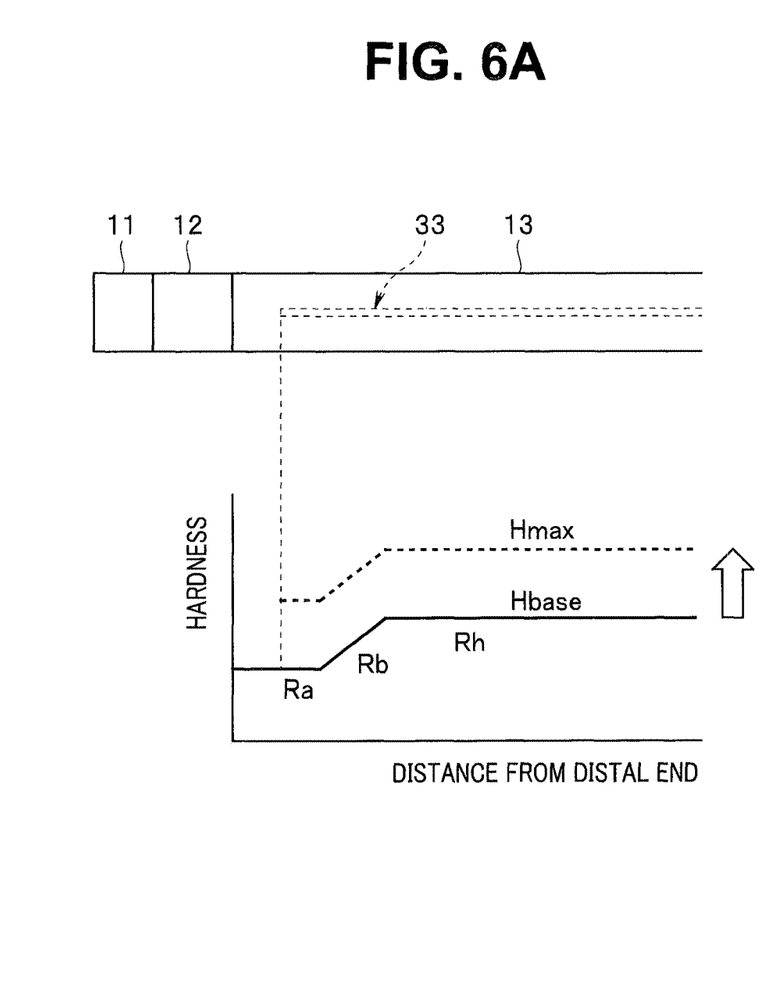
FIG. 6A is an explanatory diagram illustrating a hardness characteristic of a flexible tube portion.

The flexible tube portion 13 of the endoscope 2 is set to a hardness characteristic as shown in FIG. 6A. FIG. 6A illustrates a distribution of hardness H versus a distance L from the distal end of the flexible tube portion 13; a solid line of the graph representing base hardness Hbase of the flexible tube portion 13 in a flexible state when the hardness variable member 33 is not pulled (the coil pipe 34 that allows insertion of the pulling wire 35 is not pulled) and a broken line of the graph representing maximum hardness Hmax of the flexible tube portion 13 when the hardness variable member 33 is in a most compressed state (a state in which the pulling wire 35 is pulled to a maximum and the coil pipe 34 is most compressed).

Figure 6B:
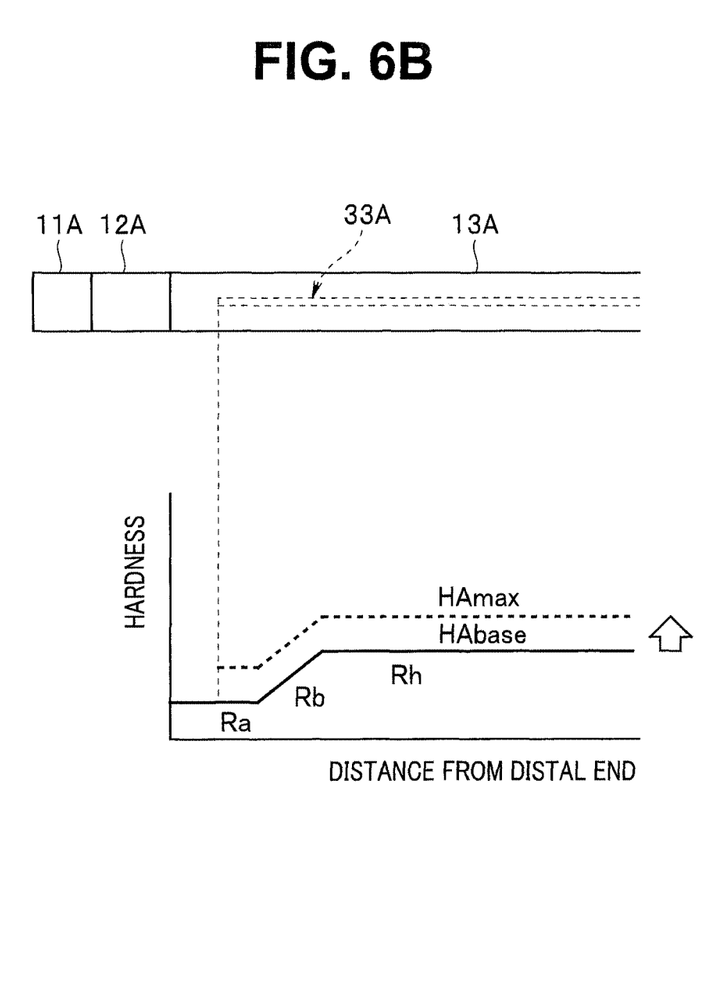
FIG. 6B is an explanatory diagram illustrating a hardness characteristic of a flexible tube portion.

In contrast, the flexible tube portion 13A of the endoscope 2A is set to a hardness characteristic as shown in FIG. 6B. Compared to the hardness variable member 33 of the endoscope 2, when the hardness variable member of the endoscope 2A is denoted by reference numeral 33A, FIG. 6B illustrates a distribution of hardness H versus a distance L from the distal end of the flexible tube portion 13A; a solid line of the graph representing base hardness HAbase of the flexible tube portion 13A in a flexible state when the hardness variable member 33A is not pulled and a broken line of the graph representing maximum hardness HAmax of the flexible tube portion 13A when the hardness variable member 33A is in a most compressed state.

Note that the flexible tube portions 13 and 13A of the endoscopes 2 and 2A in the present embodiment are each provided with a hardness change region Rb in which hardness gradually changes from a flexible region Ra on the distal end side from a most flexible state to a hardest state, and the proximal end side of the hardness change region Rb constitutes a rigid flexible region Rh in which hardness becomes the hardest state. The distal end portion of the coil pipe 34 inserted through the flexible tube is disposed in a flexible region Ra closer to the distal end side than the hardness change region Rb.

In the hardness characteristics shown in FIG. 6A and FIG. 6B, a hardness variation (Hmax−Hbase) of the flexible tube portion 13 of the endoscope 2 and a hardness variation (HAmax−HAbase) of the flexible tube portion 13A of the endoscope 2A are set such that respective ratios K against the base hardness are constant. The ratio K is set, for example, to approximately K=0.5 (50%) and is set to a common constant proportion among a plurality of endoscopes.

That is, a relationship between a hardness variation and base hardness among a plurality of endoscopes with flexible tube portions having different outer diameters is such a relationship as shown in the following equation, where the hardness variation is represented by $\Delta H$ and base hardness is represented by Hb.

$$\Delta H = K \times Hb$$

That is, the thicker the flexible tube portion becomes, the greater the hardness variation becomes, and the hardness variation of an endoscope with a relatively thin flexible tube portion is also small, and the hardness variation in that case becomes a constant proportion with respect to a variation (variation of base hardness) of the thickness of the flexible tube portion. For example, when the outer diameter of the flexible tube portion 13 of the endoscope 2 is double the outer diameter of the flexible tube portion 13A of the endoscope 2A (base hardness is double), the hardness variation of the flexible tube portion 13 of the endoscope 2 is double the hardness variation of the flexible tube portion 13A of the endoscope 2A, which is the same ratio as the variation of the thickness of the flexible tube (variation of base hardness).

In this way, it is possible to avoid situations like an endoscope with a thick flexible tube portion lacking hardness or an endoscope with a thin flexible tube portion becoming too hard, and eliminate a sensory gap between a difference in thickness of the flexible tube portion and a difference in hardness variation and provide an optimal insertion operation. In the case of an endoscope with a thick flexible tube portion, it is possible to perform a speedy operation by minimizing warpage and in the case of an endoscope with a thin flexible tube portion, it is possible to perform a refined operation by suppressing hardness to a minimum level.

In order to acquire the hardness characteristic described above, the hardness change mechanism 50 is set such that the conditions shown in (1) to (4) below correlate to each other with respect to the magnitude relationship of the outer diameters of the flexible tube portions. The conditions may be applied singly or in combination.

(1) Diameter of the Coil Elemental Wire

When the diameter of the elemental wire of the coil pipe 34 is assumed to be d, by changing the diameter of the elemental wire d in accordance with the thickness of the flexible tube portion, the diameter d is adjusted so as to obtain the characteristics shown in FIG. 6A and FIG. 6B. For example, when a coil diameter D of the coil pipe 34 is assumed to be constant as shown in FIG. 7A and FIG. 7B, the hardness variation of the flexible tube portion is reduced by adopting a smaller wire diameter of the elemental wire d' (d'<d) as the flexible tube portion becomes thinner.

(2) Coil Diameter

By changing the coil diameter of the coil pipe 34 in accordance with the thickness of the flexible tube portion, the coil diameter is adjusted so as to obtain the characteristics shown in FIG. 6A and FIG. 6B. For example, as shown in FIG. 7B and FIG. 7C, when the diameter of the elemental wire d' of the coil pipe 34 is assumed to be constant, the hardness variation of the flexible tube portion is reduced by adopting a smaller coil diameter D' (D'<D) as the flexible tube portion becomes thinner.

Figure 7A:
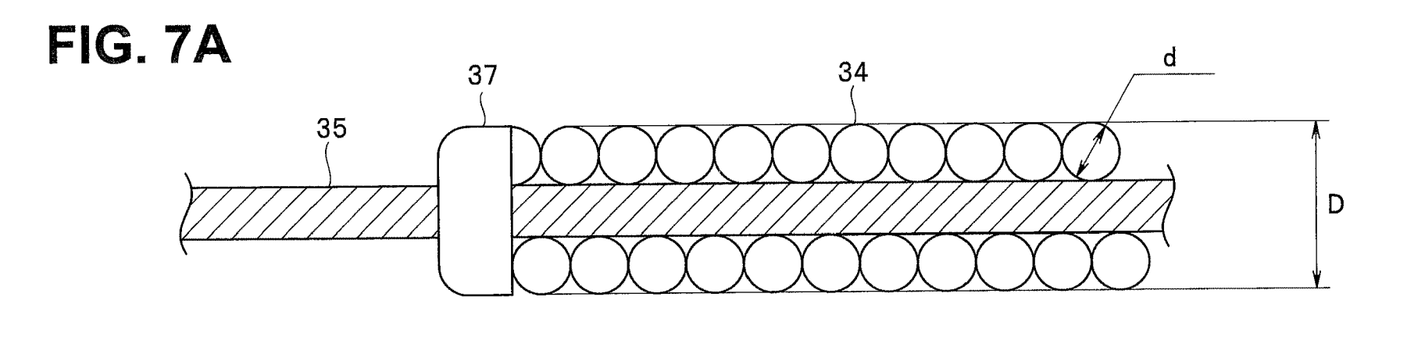
FIG. 7A is an explanatory diagram illustrating an adjustment of a hardness characteristic according to an elemental wire diameter and a coil diameter of a coil pipe.
Figure 7B:
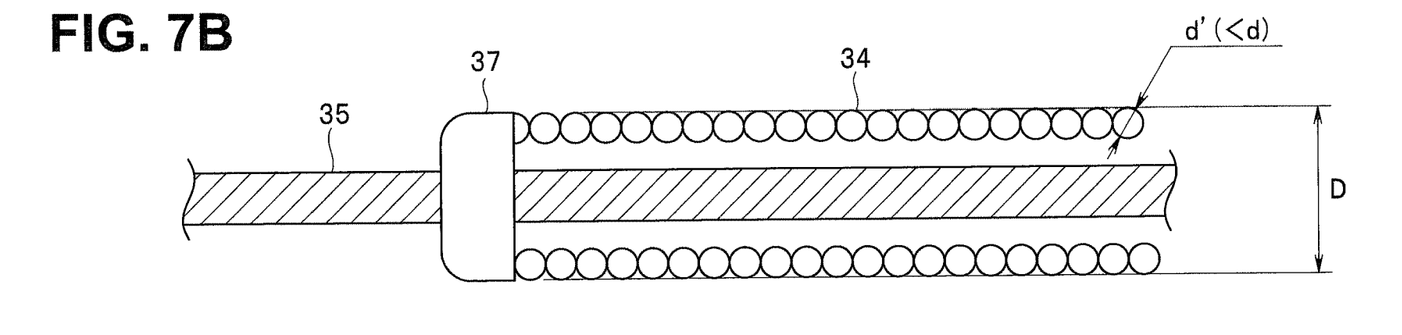
FIG. 7B is an explanatory diagram illustrating an adjustment of a hardness characteristic according to an elemental wire diameter and a coil diameter of a coil pipe.
Figure 7C:
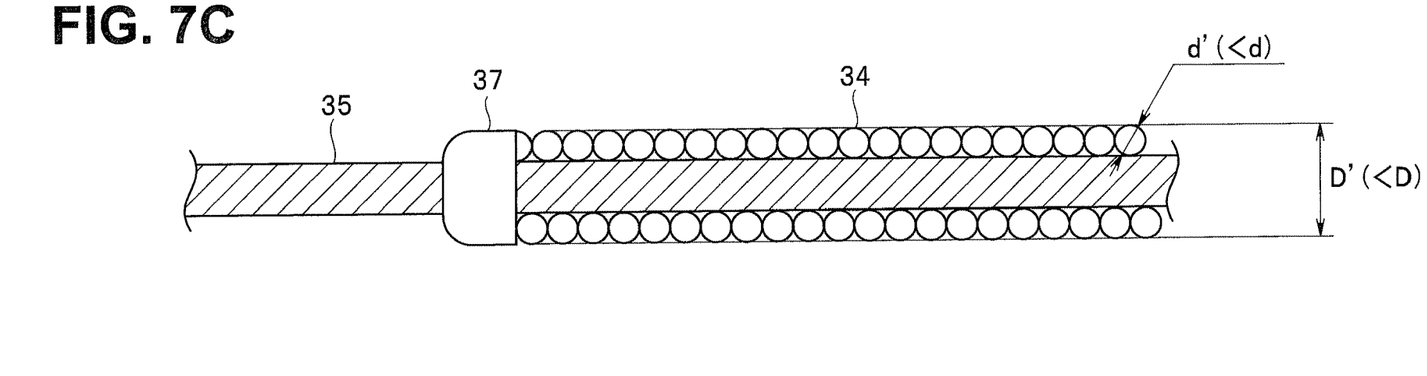
FIG. 7C is an explanatory diagram illustrating an adjustment of a hardness characteristic according to an elemental wire diameter and a coil diameter of a coil pipe.

Note that in FIGS. 7A to 7C, the coil pipe 34, the pulling wire 35 and the cap 37 are only different in size, and the same reference numerals are therefore assigned for convenience. The same applies to FIGS. 8A to 8C which will be described later.

In this case, the conditions in (1) and (2) may be adjusted so as to obtain the characteristics shown in FIG. 6A and FIG. 6B by changing both the diameter of the coil elemental wire and the coil diameter instead of individually applying the respective conditions. For example, as in the cases of FIG. 7A and FIG. 7C, both the coil diameter and the diameter of the coil elemental wire may be reduced as the flexible tube portion becomes thinner, and it is thereby possible to further increase the degree of freedom in setting hardness characteristics.

Thus, when adjusting the hardness characteristics by changing the diameter of the coil elemental wire and the coil diameter of the coil pipe 34, the outer diameter and the diameter of the elemental wire of the coil pipe 34 are changed in accordance with the thickness of the flexible tube portion. This leads to optimization of a filling factor of internal components of the flexible tube portion and can also prevent an adverse effect on other internal components.

(3) Wire Diameter

Figure 8A:
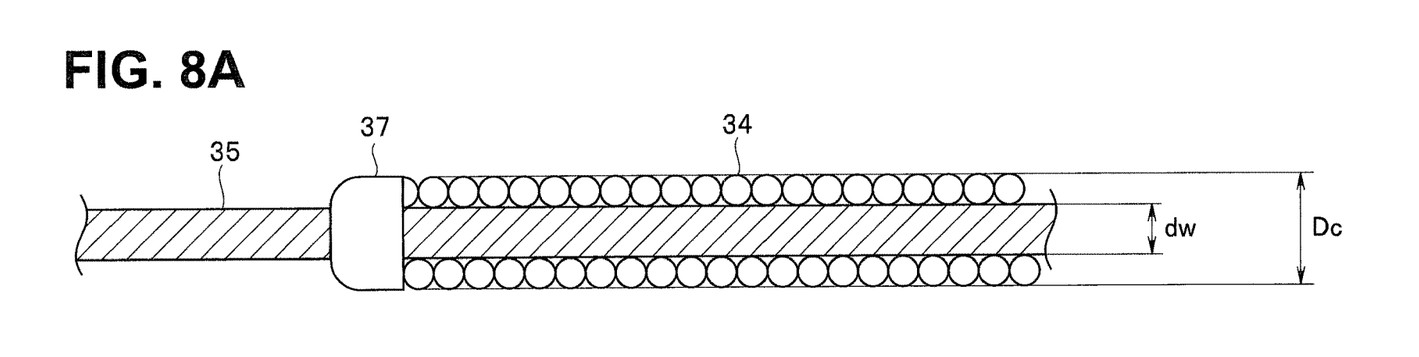
FIG. 8A is an explanatory diagram illustrating an adjustment of a hardness characteristic according to a wire diameter of a pulling wire.
Figure 8B:
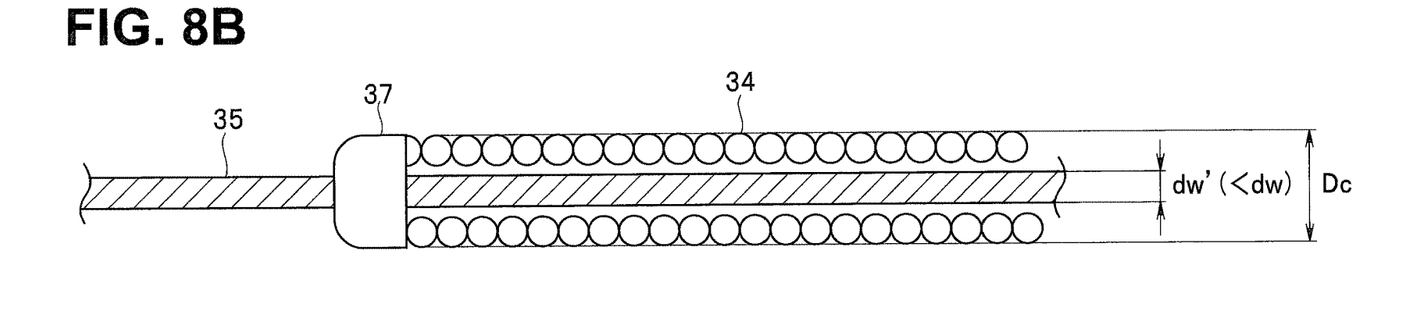
FIG. 8B is an explanatory diagram illustrating an adjustment of a hardness characteristic according to a wire diameter of a pulling wire.

By changing the wire diameter of the pulling wire 35 in accordance with the thickness of the flexible tube portion, the wire diameter is adjusted so as to obtain the characteristics shown in FIG. 6A and FIG. 6B. For example, when the coil diameter of the coil pipe 34 is assumed to be a constant coil diameter Dc as shown in FIG. 8A and FIG. 8B, a wire diameter dw of the pulling wire 35 is assumed to be a smaller wire diameter dw' (dw'<dw) and the hardness variation of the flexible tube portion is reduced as the flexible tube portion becomes thinner. Furthermore, as in the cases in FIG. 8A and FIG. 8C, both the coil diameter and the wire diameter may be reduced as the flexible tube portion becomes thinner.

Figure 8C:
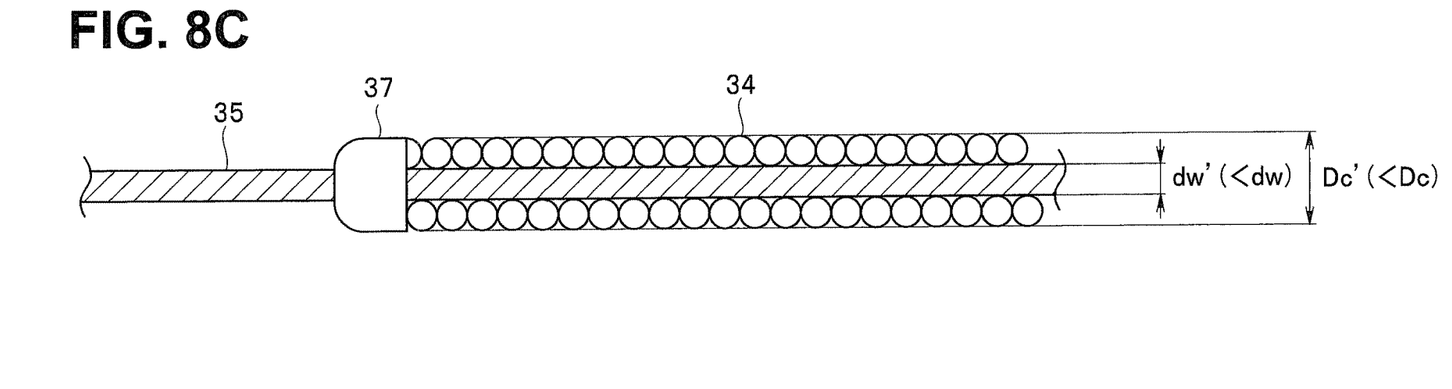
FIG. 8C is an explanatory diagram illustrating an adjustment of a hardness characteristic according to a wire diameter of a pulling wire.

Note that FIGS. 8A to 8C illustrate cases where the diameter of the coil elemental wire of the coil pipe 34 is constant, but the diameter of the coil elemental wire, the coil diameter and the wire diameter may be changed in accordance with the thickness of the flexible tube portion.

(4) Amount of Wire Pulling

By changing the amount of wire pulling of the pulling wire 35 in accordance with the thickness of the flexible tube portion, the amount of wire pulling is adjusted so as to obtain the characteristics shown in FIG. 6A and FIG. 6B. The amount of wire pulling can be changed, for example, by changing the shapes of the cam grooves 45a and 45b of the cam cylindrical body 45 shown in FIG. 3. The amount of wire pulling is relatively reduced and the hardness variation of the flexible tube portion is reduced as the flexible tube portion becomes thinner.

In this case, both the wire diameter and the amount of wire pulling may be changed in accordance with the thickness of the flexible tube portion. Generally, durability degrades as the wire diameter of the pulling wire 35 is reduced, and so the amount of wire pulling cannot be increased so much, but durability can be improved by reducing the amount of wire pulling. Furthermore, all the diameter of the coil elemental wire, the coil diameter, the wire diameter and the amount of wire pulling may be changed.

Thus, according to the present embodiment, in a plurality of types of endoscopes with flexible tube portions having different hardness (thickness) levels, hardness variations of the respective flexible tube portions are set so as to be in direct proportion to base hardness before changing hardness and the ratios against the hardness of the flexible tube portions are unified. In this way, it is possible to implement an endoscope system capable of unifying feelings of use among endoscopes with flexible tubes having different hardness (thickness) levels and obtaining optimum insertion performance.

What is claimed is:

1. An endoscope system comprising:
   a first endoscope comprising:
      a flexible first insertion portion; and
      a first hardness change mechanism provided to be operable within the first insertion portion by operating a first hardness operation portion provided on a proximal end side of the first insertion portion, the first hardness change mechanism being configured to change a hardness of the first insertion portion between a first minimum hardness and a first maximum hardness; and
   a second endoscope comprising:
      a second flexible insertion portion; and
      a second hardness change mechanism provided to be operable within the second insertion portion by operating a second hardness operation portion provided on a proximal end side of the second insertion portion, the second hardness change mechanism being configured to change a hardness of the second insertion portion between a second minimum hardness which is greater than the first minimum hardness and a second maximum hardness which is greater than the first maximum hardness,
   wherein the first hardness change mechanism and the second hardness change mechanism each comprise:
      a coil pipe, a wire inserted into the coil pipe, a distal end side of the wire being fixed to the coil pipe, and a pulling mechanism comprising a pulling member configured to move the wire in a direction by pulling a proximal end side of the wire by operation of the hardness operation portion, the pulling mechanism being configured to move the wire in the direction such that the coil pipe fixed to the wire is contracted, and in each of the first hardness change mechanism and the second hardness change mechanism, at least one of a coil diameter of the coil pipe, an elemental wire diameter of the coil pipe, a wire diameter of the wire and a pulling amount of the wire are configured such that a second hardness variation of the second insertion portion between the second minimum hardness and the second maximum hardness is greater than a first hardness variation of the first insertion portion between the first minimum hardness and the first maximum hardness.

2. The endoscope system of claim 1, wherein a first ratio of the second hardness variation and the first hardness variation is proportional to a second ratio between a diameter of the second insertion portion and a diameter of the first insertion portion.

* * * * *